(12) United States Patent
Shalom

(10) Patent No.: US 7,146,650 B2
(45) Date of Patent: Dec. 12, 2006

(54) EAR COVERS

(75) Inventor: Isaac Shalom, New York, NY (US)

(73) Assignee: New York Accessory Group, New York, NY (US)

(*) Notice: Subject to any disclaimer, the term of this patent is extended or adjusted under 35 U.S.C. 154(b) by 48 days.

(21) Appl. No.: 10/892,726

(22) Filed: Jul. 16, 2004

(65) Prior Publication Data

US 2006/0010581 A1    Jan. 19, 2006

(51) Int. Cl.
*A42B 1/06*    (2006.01)

(52) U.S. Cl. .......................... 2/209; 381/370; 381/371; 181/129

(58) Field of Classification Search ............... 2/208, 2/209, 423; 381/370, 371; 181/129; 179/156
See application file for complete search history.

(56) References Cited

U.S. PATENT DOCUMENTS

| | | | | |
|---|---|---|---|---|
| 2,361,963 A | * | 11/1944 | Rosenblatt | 181/22 |
| 2,609,544 A | * | 9/1952 | Berg | 2/209 |
| 3,447,160 A | * | 6/1969 | Teder | 2/209 |
| 4,037,273 A | * | 7/1977 | Labaire | 2/209 |
| 4,524,803 A | * | 6/1985 | Stoll et al. | 137/625.64 |
| 4,546,215 A | * | 10/1985 | Ferraro | 381/374 |
| 4,654,898 A | * | 4/1987 | Ishikawa | 2/209 |
| 5,835,609 A | | 11/1998 | LeGette et al. | 381/187 |
| 6,016,574 A | * | 1/2000 | Chen | 2/209 |
| 6,322,223 B1 | | 11/2001 | Le Gette et al. | 2/209 |
| 6,499,146 B1 | | 12/2002 | Bavetta et al. | 2/209 |
| 6,502,247 B1 | | 1/2003 | Le Gette et al. | 2/209 |
| 6,502,248 B1 | | 1/2003 | LeGette et al. | 2/209 |
| 6,735,784 B1 | | 5/2004 | Isom et al. | 2/209 |

* cited by examiner

*Primary Examiner*—Katherine Moran
*Assistant Examiner*—Richale L. Haney
(74) *Attorney, Agent, or Firm*—Ostrolenk, Faber, Gerb & Soffen, LLP

(57) ABSTRACT

Ear covers and a strap for joining the ear covers. Each ear cover includes an inner cup over the ear, an outer cup over the inner cup. The cups are shaped to define an inner space between them in which an end region of the strap is guided to move lengthwise with respect to the ear cover. A channel on the outside of the inner cup receives a flange on the strap for guiding its longitudinal movement. The rims of the inner and the outer cups are connected and a protective covering cloth may be at the rims for contacting the user's head around the ear.

6 Claims, 2 Drawing Sheets

EAR COVERS

BACKGROUND OF THE INVENTION

The present invention concerns ear covers and particularly ear covers including a cup over each ear and the cups joined by a connector.

Ear covers are typically worn to protect the ears from cold air or a cold environment or for affecting or providing sound received by the ear. Typical ear covers are shaped to cover the ear. The two covers are typically joined by a connector that extends between the ear covers and wraps either over the top of the head or behind the head and holds the ear covers to the ears by elastically biasing the ear covers toward each other.

The ear covers may have many different forms, including a pad of material with an inward side, and perhaps carrying an inward covering that faces toward and may be pressed against the ear and an outward side that may be covered with a decorative covering, e.g., fur.

Some ear covers, such as ear phones used for delivery of audio, are not flat and do not press against the ear on the inward side of the cover, but rather define a cup shaped chamber over the ear. The present invention is concerned with this type of ear covers.

A connector between the two ear covers may be of a resilient metal, plastic material or a like function material and has an initial shape to bias the ear covers toward each other, such that when the covers are separated to be placed over the ears, the connector urges the ear covers securely against the ears or the head. Since heads are of different sizes and widths, ears are slightly differently located on different people, and people have different comfort levels, there is typically some adjustment of the position of one or both of the cups with reference to the connector or adjustment of the connector itself that increases or decreases the effective length of the connector, perhaps to accommodate each head size or to reposition the ear covers at the ears. In typical ear covers, the adjustment is made at the connector by adjusting the length of the connector or by adjusting the positions of the ear covers on the connector. The invention concerns the latter type of adjustment.

SUMMARY OF THE INVENTION

It is an object of the present invention to provide ear covers which may be comfortable to wear. Another object of the invention is to enable adjustment of the ear covers to requirements of an individual user.

According to the invention, a pair of ear covers are joined by a connector in the form of a resilient strap that urges the ear covers against the head.

Each ear cover comprises a stiff, perhaps molded plastic, inner cup which is sized and shaped to define a chamber which encloses the typical ear wholly within the chamber. The cup has an outer peripheral rim which is pressed toward the wearer's head around the ears in the chamber. There may be a comfort cushion of a fabric, fur, simulated fur, or the like on the inside of the inner cup which contacts the ear and is both comfortable and provides extra temperature protection.

The cover comprises another stiff, perhaps molded plastic, shaped outer cup disposed outward of and over the inner cup with a slightly larger chamber than the inner cup to define a short height space or chamber between the inner and the outer cups which provides a space for receiving the below described strap between the inner and the outer cups. The outer cup also has a peripheral rim. The inner and the outer cups are preferably shaped so that they meet around their peripheries. An appropriate securement is applied between them at their peripheries. That securement may be a clip at one of the inner and the outer cups to hold them together. When the ear cover contacts the user's head where the inner and the outer cups are joined, a peripheral or annular shaped contact element passes around the peripheries of the cups and where they were pressed against the head to provide an air and environment guard for protecting the ear and to provide the user comfort. This contact element may be a cloth or a cushioned layer of cloth, or the like. The exterior of the outer cup may be appropriately decorated.

For wearing comfort, there may be perforations in the inner and the outer cup to allow some air circulation, avoid overheating and enable ambient noise to enter.

The strap that connects to each ear cover is of a resilient material and has a respective end region that is joined to each ear cover. The end region of the strap passes through an opening in the outer cup and enters the space between the inner and the outer cups. The inside of the outer cup and/or the outside of the inner cup in the chamber between the cups is shaped and the strap is so shaped that one or both of the cups holds the strap and guides its movement in that space, and the movement of the strap adjusts the position of the ear cover along the strap. There is a corresponding guide for the strap on either the exterior of the inner cup, or on the interior of the outer cup so that the strap is guided in the space between the inner and the outer cups.

The strap is prevented by the inner cup from moving inward to the ear and by the outer cup from moving outwardly away from the ear. To also guide the strap against moving laterally or generally parallel to the ear, there is a strap motion guide on at least one of the inner and the outer cups and a cooperating guide on the strap which guides the strap to move only along its length in the space between the cups and not move laterally. In a preferred embodiment, there is a shaped projection at the end region of the strap and a cooperating guide channel on the outside of the inner cup, in which the strap is disposed and which guides the strap to move lengthwise and prevents it from moving laterally in the space between the inner and the outer cups. The strap may be appropriately decorated.

Other objects and features of the present invention are described below in connection with the accompanying drawings.

DETAILED DESCRIPTION OF PREFERRED EMBODIMENTS

Figure 1:
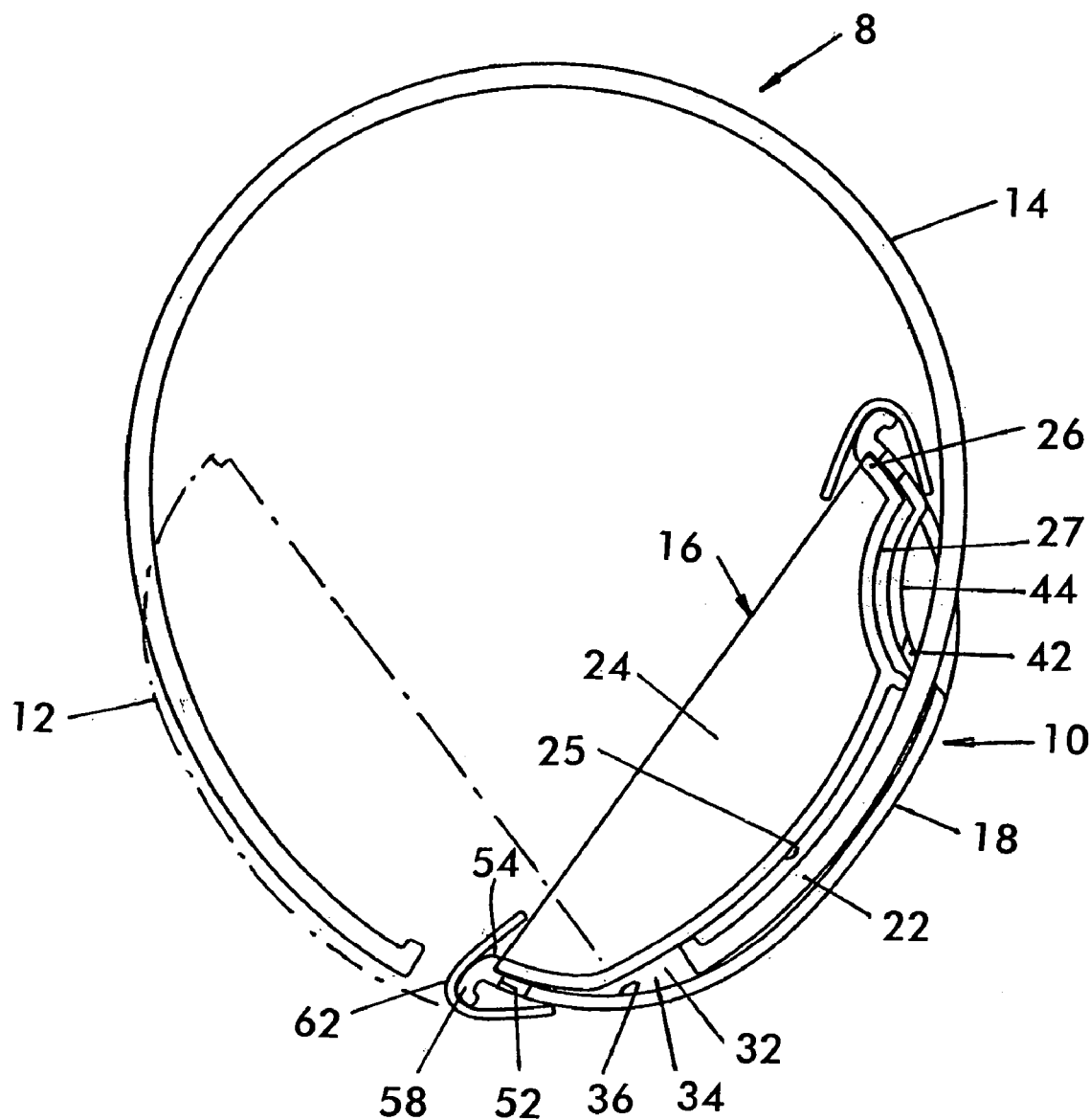
FIG. 1 is a side cross-sectional view of a pair of ear covers, showing details of one ear cover for connection to a strap.
Figure 2:
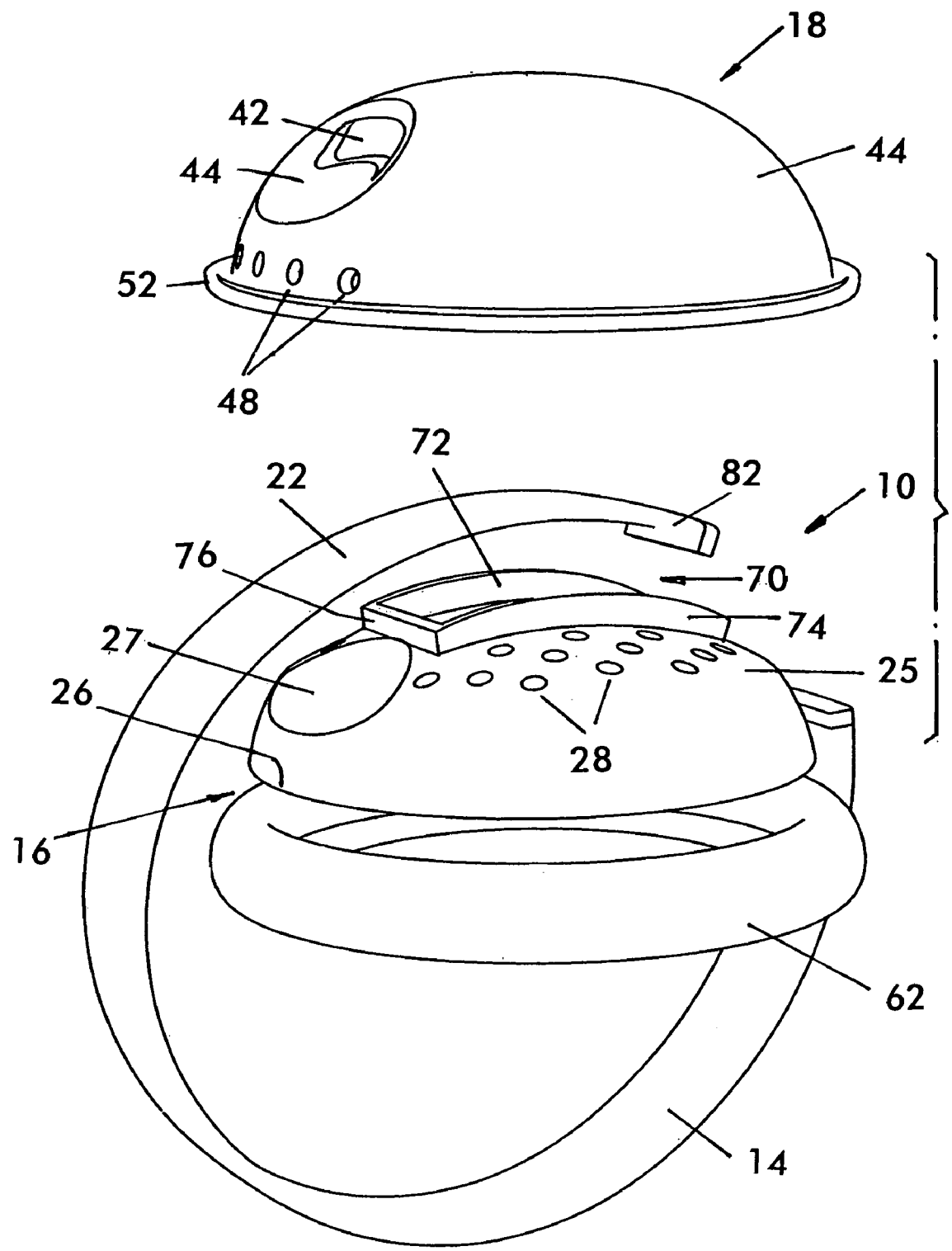
FIG. 2 is a perspective view of the one ear cover and the strap.

Ear covers 8 according to the present invention are comprised of first ear cup 10 and second ear cup 12, shown in phantom, and a connector in the form of a strap 14 which joins the ear covers 10 and 12. Only one ear cover 10 is shown and described in detail, it being understood that the other ear cover 12 would be identical.

The cup 10 is comprised of a cooperating inner cup 16 and outer cup 18 which cooperate with a respective end region 22 of the strap 14 for retaining the ear cover 10 on the strap 14.

The inner cup 16 is generally cup shaped or shell shaped with a hollow cup shaped interior chamber 24 as defined inside and by the peripheral rim 26 of the cup 16. The rim 26 and the cup chamber 24 are so dimensioned and shaped as to enable the rim 26 to completely encircle a normal ear and for the rim to be pressed against the head around the enclosed chamber 24 over the ear. The inner cup may have small perforations 28 to allow escape of body heat and water vapor to maintain a user's comfort level and for passage of ambient noise.

Outward of the inner cup 16 is the outer cup 18 which is shaped with its own internal chamber 32 that is deeper than the chamber 24 of the inner cup. This difference defines the narrow height space 34 between the outside 25 of the inner cup 16 and the inside 36 of the outer cup. The cups 16 and 18 are shaped at their sides 25 and 36 to define the space 34 of a height that guides movement of the end region 22 of the strap, as discussed below.

The outer cup includes a passage opening 42 through a side thereof which opening is sized and shaped to receive the end region 22 of the strap and to serve as a guide for orienting the strap with respect to the ear cover. For better positioning the strap and for aesthetic reasons, the exterior of the outer cup 18 has a shallow recess 44 through which the passage opening 42 passes. The recess 44 enables that area 42 to be more directly at least nearly transverse to the strap so that the opening 42 can be shorter in height than it would have to be if there were no such recess 44.

The exterior 25 of the inner cup has a recess 27 shaped to cooperate with the recess 44 in the outer cup. The cooperating recesses also aid easy orientation of the outer and inner cups with respect to each other during assembly of the ear cover.

For providing ventilation and noise access, the outer cup 18 has its own set of perforations 48.

The outer cup terminates in its own periphery 52. At the periphery 52, there is an attachment rim 54 which is shaped to enable the outer cup to be pressed on and over the periphery of the inner cup and then to snap under the periphery of the inner cup, as shown in FIG. 1, thereby securing the outer cup to the inner cup. Their respective cup profiles keep the cups in the orientation obtained by the cooperation of the rim clip with the rim 26 of the inner cup. Since the peripheral region of the ear cover is the part pressed against the user's head, the outer cup may have a widened peripheral band 58 to spread the contact pressure on the head. The inward facing side of the band 58 may be covered by a decorative cloth 62, or appropriate cushioning material, or the like to enhance user comfort.

The end region 22 of the strap is of the same width, height, and cross-section as the remainder of the strap or may be otherwise shaped. The height of the space 34 between the outer surface 25 and the inner surface 36 is selected so that the end region 22 will be guided between them and be prevented by the inner cup from moving from inward toward the user's ear and by the outer cup from moving outward or away from a user's ear. The cups do not interfere with movement of the strap 14 along its length with respect to the ear cover.

A longitudinal movement guide for the end region 22 of the strap is provided. As shown, it comprises a channel 70 attached to or integrally formed with or molded with the outside 25 of inner cup 16. The channel 70 includes opposing upstanding walls 72, 74 and an end terminal wall 76 which prevents the strap from being pulled out from the ear cover through the opening 42.

The end region 22 of the strap 14 has a cooperating projection or flange 82 that is of the width between the walls 72 and that rides in the channel 70 as the strap 14 is moved lengthwise through the ear cover. The walls 72 are of such height as to establish a minimum height for the chamber 34 in which the strap moves and also to prevent the flange 82 from moving out of the channel 70. Alternative guide arrangements within this concept would include a channel, like channel 70, defined on the inside of the outer cup, rather than on the inner cup, and with the strap having an appropriate flange or other fixture cooperating with the guide in the outer cup, or guides in both cups. Alternatively, it is possible for the guide channel to be defined on the strap and for a flange or protrusion to be defined on one of cups. Other longitudinal guide arrangements for the strap may be provided to guide its movement with respect to the cups.

The exterior of the outer cup may be decorated in some manner with an appropriate decorative covering. An appropriate additional fabric layer not shown may be disposed inside the inner cup to rest against the ear.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An ear cover and strap combination, comprising:
    a strap for supporting at least one ear cover, the strap having an end region for being received at the ear cover and for supporting the ear cover;
    an ear cover comprised of an inner cup having a shape to define an inwardly facing chamber that may be placed over a wearer's ear, the inner cup being defined by a first rim adapted to be disposed at the user's ear;
    an outer cup disposed outward of the inner cup, the outer cup being shaped to have a second rim which extends to generally meet with the first rim of the inner cup to together define the ear cover from the outer and the inner cups;
    the inner cup having an outward facing side, the outer cup defining a chamber having an inward facing side in opposition to the outward facing side of the inner cup, and the inner and the outward facing cups being so shaped as to define a space of a first height between the outward facing side of the inner cup and the inward facing side of the outer cup;
    the end region of the strap extending from outside the ear cover into the inner space of the ear cover between the inner cup and the outer cup;
    the space being so sized and the inner cup and the outer cup being so shaped and the strap being so shaped and sized that the strap is guided to move along the length of the strap with respect to the ear cover through the space, enabling adjustment of the position of the ear cover along the strap;
    respective guide elements between the strap in the space and at least one of the cups for guiding movement of the strap with respect to the ear cover for guiding the movement of the strap along its length in the space, the guide elements comprise a channel on the outer side of the inner cup and an element on the strap which rides in the channel for guiding the element on the strap to move with respect to the inner cup through the space.

2. The combination of claim 1, further comprising an opening through the outer cup into the space and the strap passing from outside the ear cover into the space inside the ear cover through the opening.

3. The combination of claim 1, further comprising a material layer generally at the rims of the cups for providing contact area between the rims and a wearer's head around the ear.

4. The combination of claim 1, further comprising a connection at the rims of the inner and the outer cups for enabling the outer cup to be disposed over the inner cup and to be connected to the inner cup at least at the rims thereof with the space defined between the inner and the outer cups.

5. The combination of claim 1, wherein the inner and the outer cups are so shaped that they together define part of the guide elements for the longitudinal movement of the strap with reference to the ear cover and the space.

6. The combination of claim 1 further comprising the strap having a second end region; a second one of the ear covers disposed at the second end region of the strap.

* * * * *